United States Patent [19]
Albrektsson et al.

[11] Patent Number: 6,102,954
[45] Date of Patent: Aug. 15, 2000

[54] JOINT PROSTHESIS AND APPARATUS FOR PREPARING THE BONE PRIOR TO FITTING OF THE PROSTHESIS

[75] Inventors: Björn Albrektsson, Onsala; Lars Valter Carlsson, Kullavik; Carl Magnus Gösta Jacobsson, Göteborg; Tord Valter Röstlund, Kullavik; Stig Gösta Wennberg, Angered, all of Sweden

[73] Assignee: Astra Aktiebolag, Sodertalje, Sweden

[21] Appl. No.: 08/804,675

[22] Filed: Feb. 25, 1997

Related U.S. Application Data

[63] Continuation of application No. 08/338,623, Dec. 16, 1994, abandoned.

[30] Foreign Application Priority Data

May 18, 1992 [SE] Sweden .................................. 9201557

[51] Int. Cl.⁷ .................................................. A61F 2/38
[52] U.S. Cl. .......................................................... 623/20
[58] Field of Search ........................................ 623/20, 18

[56] References Cited

U.S. PATENT DOCUMENTS

| 4,919,671 | 4/1990 | Karpf ........................................ 623/20 |
| 5,047,058 | 9/1991 | Roberts .................................... 623/20 |
| 5,092,895 | 3/1992 | Albrektsson .............................. 623/20 |

FOREIGN PATENT DOCUMENTS

| 2630639 | 11/1989 | France ...................................... 623/20 |
| 2676916 | 12/1992 | France ...................................... 623/20 |
| 2691356 | 11/1993 | France ...................................... 623/20 |
| 719625 | 3/1980 | U.S.S.R. .................................... 623/20 |
| 2061730 | 5/1981 | United Kingdom ..................... 623/20 |

*Primary Examiner*—Michael J. Milano
*Attorney, Agent, or Firm*—White & Case LLP

[57] ABSTRACT

The invention relates to a prosthesis for uni-condylar or bi-condylar replacement of a joint in a human body and in particular to the tibia side of a knee joint. By means of an elongate fixture, a prosthetic plate is secured in position in a pre-prepared tibia portion and is allowed to heal, without further surgery being required. The invention also relates to a device for preparing the knee joint for prosthetic reception.

23 Claims, 10 Drawing Sheets

JOINT PROSTHESIS AND APPARATUS FOR PREPARING THE BONE PRIOR TO FITTING OF THE PROSTHESIS

This application is a continuation of application Ser. No. 08/338,623, filed on Dec. 16, 1994, now abandoned.

DESCRIPTION

The invention relates to a joint prosthesis for permanent anchorage in the bone tissue of one of the articulatory parts of a joint in the human body, in particular the tibia side of a knee joint, wherein the prosthesis comprises a flat, plate-like element having an elongate fixture portion. The invention also relates to an apparatus for preparing said joint for acceptance of the said prosthesis.

The reasons for surgical replacement of articulatory parts of knee joints or other joints and the various methods adopted are to some extent summarised in the introductory portion of published European Patent Application EP-A-0 183 669 (priority claimed from SE 8405989). This document also discloses an example of an improved method for replacing a joint and a joint prosthesis for fitting to human body joints, in particular to knee joints. The method adopted in that application is to perform two successive operations (a so-called two-seance procedure) on the subject. In the first operation an anchoring element is fixed into one or both sides of a knee joint i.e. the tibia (shin side) and femur (thigh side) and then allowed to integrate into the bone tissue (so-called osseointegration). Once firmly anchored (after about 6 weeks) a second operation is performed, whereby articulation members are firmly attached to the anchoring members.

Whilst this method is clearly successful, it suffers from the drawback that the patient must be subjected to two individual successive operations, in order that full unloaded osseointegration can occur. Moreover, the bone cutting operations required are fairly complex.

The present invention provides a solution to these drawbacks by providing a joint prosthesis, the essential features of which are defined in claim 1 and by providing an apparatus for preparation of the joint for allowing fitting of the prosthesis, the essential features of the apparatus being defined in claim 16.

Preferred features of the invention are defined in the dependent claims.

Whilst the following explanation relates particularly to the tibial side of a knee joint it should be understood that a similar prosthesis and method of fitting the same can of course be adapted to other joints.

With the joint prosthesis according to the invention only one major surgical operation is required, during which the knee joint is prepared in a simple yet accurate manner and then fitted with a knee joint prosthesis which is firmly secured. osseointegration and full healing can then take place without the need for further surgery.

The invention relates, in one embodiment, to a uni-condylar prosthesis and in another embodiment to a bi-condylar prosthesis, although the principles of fixation are similar in both cases.

BRIEF DESCRIPTION OF THE DRAWINGS

The principles, further preferred features and particular advantages of the invention are best described in conjunction with the attached drawings in which.

DETAILED DESCRIPTION OF PREFERRED EMBODIMENTS OF THE INVENTION

Prior to performing the fitting operation, the patient will have already undergone a pre-operational X-ray study and planning phase, during which the required measurements and parameters for the prosthesis will have been determined. The parameters arrived at allow the correct selection of dimensions for the prosthesis elements which are of course manufactured prior to the surgical operation.

Figure 1:
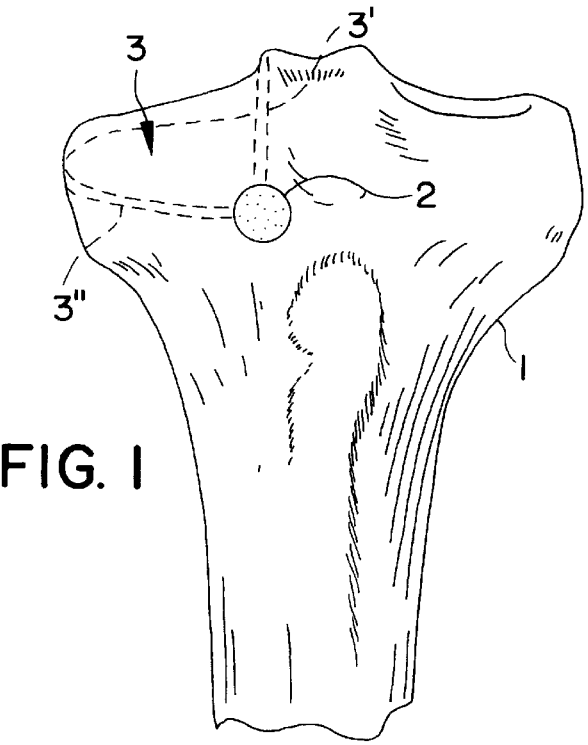
FIG. 1 depicts a top portion of a typical tibia bone to which a prosthesis is to be fitted.

FIG. 1 depicts a typical tibia bone 1 from a human leg to which a prosthesis is to be fitted. It should be understood that the bone preparation and prosthesis fitting steps described hereinafter are all carried out during one and the same surgical operation.

Firstly the tibia must be prepared before fitting of the prosthesis is possible. The first step in the operation is to drill a hole 2 all the way through the tibia starting at the front of the bone. Whilst the choice of hole bore dimension is to some extent optional within limits, a hole with approximately 8 mm diameter has been found to be satisfactory. However, the actual hole diameter chosen must be such that the hole bore closely corresponds to the diameter of the elongate fixture portion of the prosthesis replacement chosen.

One particular advantage of the invention is that the hole 2 to be drilled in the bone will be in an area of healthy bone such that good osseointegration will take place. Prior methods have meant that part of the fixture portion has often been in a portion of the bone which is not healthy.

Figure 2:
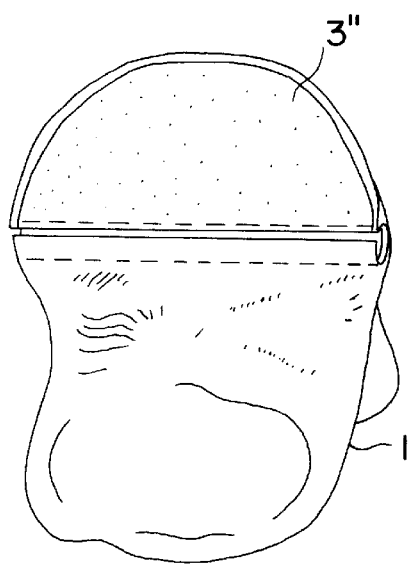
FIG. 2 depicts a plan view of the tibia of FIG. 1 after drilling, sawing and then taking out a section of the bone.
Figure 3:
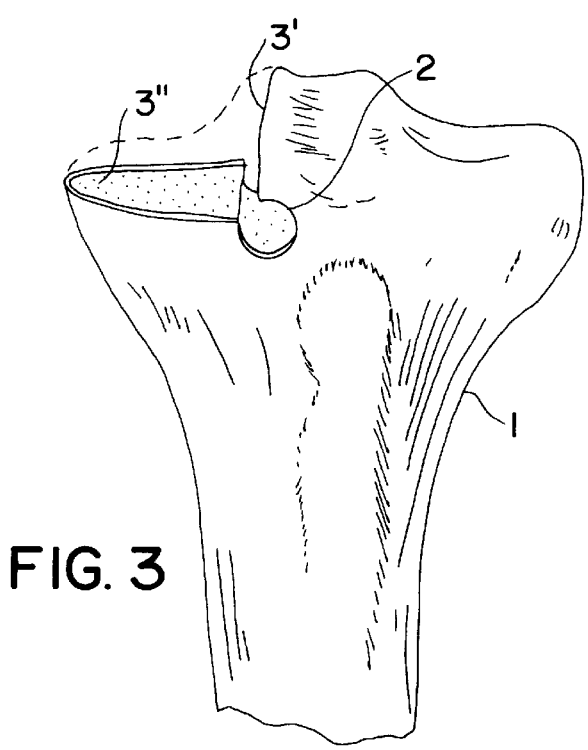
FIG. 3 depicts a side view of the tibia in FIG. 2.

The next step in the operation is to remove a uni-condylar quadrant 3 as shown in FIG. 1. The resulting bone appearance is depicted in FIGS. 2 and 3 which show respectively plan and side views of a thus-prepared tibia.

Figure 4:
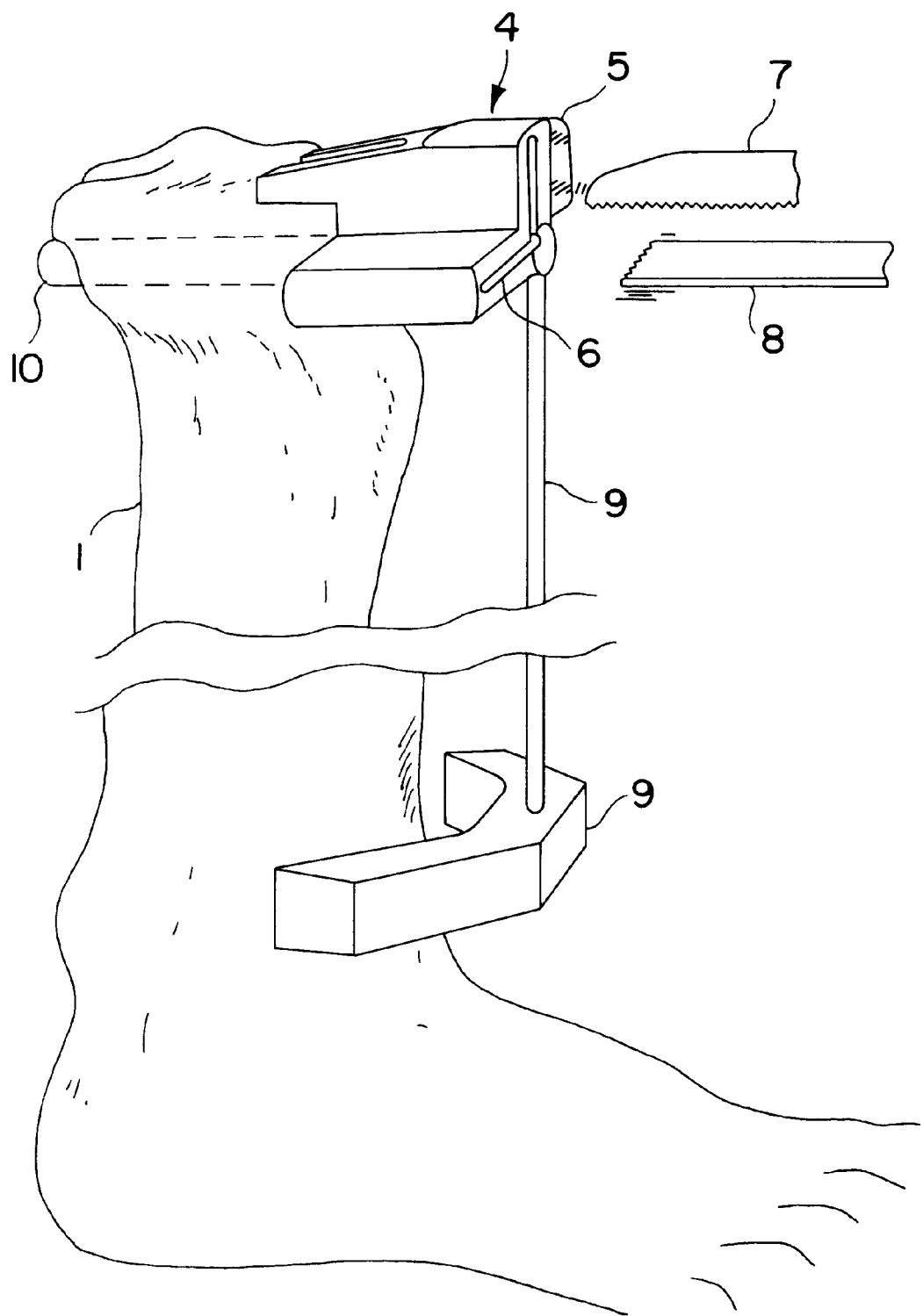
FIG. 4 depicts an embodiment of the apparatus used to cut away the section which has been removed in FIGS. 2 and 3.

The quadrant 3 can be removed by several methods but, to provide accurate guidance and to ensure that the surfaces 3' and 3" are orthogonal to each other, it is preferred to use the apparatus shown in FIG. 4 which comprises an L-shaped block 4, having vertical and horizontal slots 5, 6 therein which act as true guiding surfaces for the saw elements 7 and 8 which are used to saw out the quadrant of uni-condylar bone 3. For positioning purposes, the block 4 is of course mounted slidably on a guide 9 and clamped by a clamp 4' in position. The clamp also allows a pivotal movement of the guide rod 9 such that the lower open positioning portion 9' can be secured against the ankle part of the patient's leg. This pivotal and longitudinal freedom allows the same apparatus to be used for different leg widths and sizes.

The correct position of the saw blades in substantially vertical and horizontal directions is ensured by a further guiding device in the form of a cylindrical projection 10, formed integrally with the L-shaped block and which is a good fit in the hole 2 previously drilled in the tibia. By the combination of the elements of the apparatus of FIG. 4 a precise positioning of the saw elements is assured.

Figure 5A:
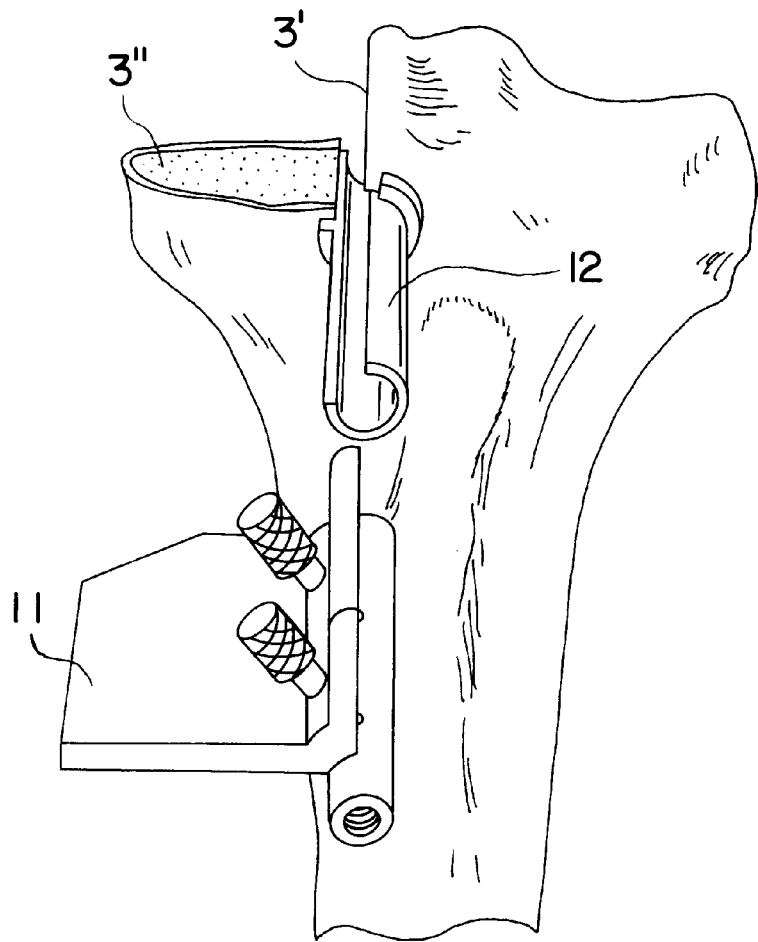
FIGS. 5(*a*), (*b*) and (*c*) show the preparation tools which are used in filing the bone surfaces and cutting of the required spline or serrated channels.

The cuts made by the saw are fairly accurate, but to provide a smooth surface to which the prosthesis is to be secured, the surfaces 3' and 3" must first be filed flat. This is performed using the file 11 shown in FIG. 5(a) which has its elongate cylindrical portion inserted into a guide element 12 placed, for this purpose, in the hole 2 already made in the tibia.

Whilst the use of splines or serrations 34, 35, 36 as will be explained hereinafter, are the most preferable embodiment of the invention it should be understood that they are not essential and that anchorage of the prosthetic plate and fixture portions by osseointegration is possible without them.

Figure 5B:
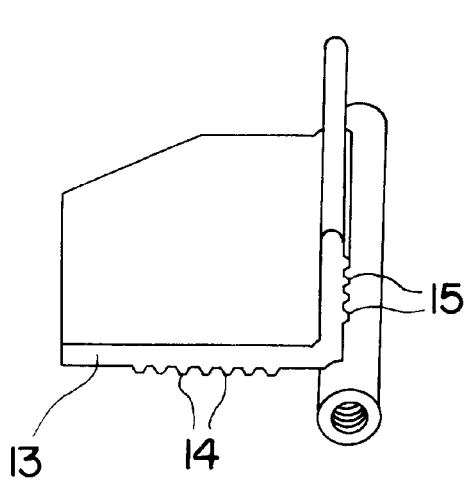
Figure 5C:
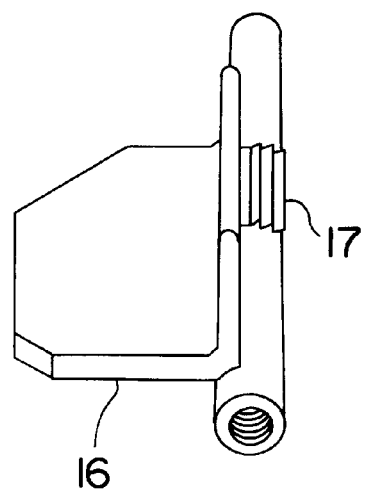

Presuming that splines are to be used, then the following sequence of cutting and preparing steps are adopted. Once the cut surfaces are sufficiently smooth, the file 11 is replaced by a further file 13, as shown in FIG. 5(b), the file having a planar lower surface provided however with spline-cutting or serration-cutting file elements 14. It is noted here for information that the splines or serrations might also be referred to as "rifling". Additionally, the file 13 is foreseen with further splines or serrations 15 attached to a vertically extending plate or flange portion.

The spline-cutting or serration-cutting surfaces 14 and 15 of the file are so arranged that the splines or serrations are cut to the required depth by a single movement of the file across the bone surfaces, such that the trailing edges of the file pass across the whole bone surface. In order to achieve this, the lower surface of the file 13 is foreseen with a series of cutting elements arranged along each of the spline-cutting surfaces 14, 15. The cutting elements will have a negative angle (i.e. they slope top-to-bottom towards the cutting direction) and will increase in depth along each of the elements 14 and 15. Thus, the height of the first cutting elements at the leading edge of the file will be minimal and the height of the cutting elements will increase successively towards the trailing edge, up to a height corresponding to the desired final spline channel depth.

With the tubular part of the file positioned in the tubular guide 12 and by the single movement of the cutting splines 14 and 15 the channels will be cut into the surface of the exposed bone until the flat plate-like parts of the file come to bear against the bone surface. After channel cutting, the file 13 and the guide 12 are removed from the hole 2.

A further file 16 is now inserted via its tubular portion into the hole 2. The cutting portions 17 on this file, similar to those on the previous file 13 are then slowly worked into the hole 2 surface whilst the horizontal and vertical plate portions of the file 16 lie against the cut surfaces 3' and 3" in order to act as guiding elements. In this manner horizontal spline channels or serrations are made in the surface of the drilled hole 2.

Figure 6:
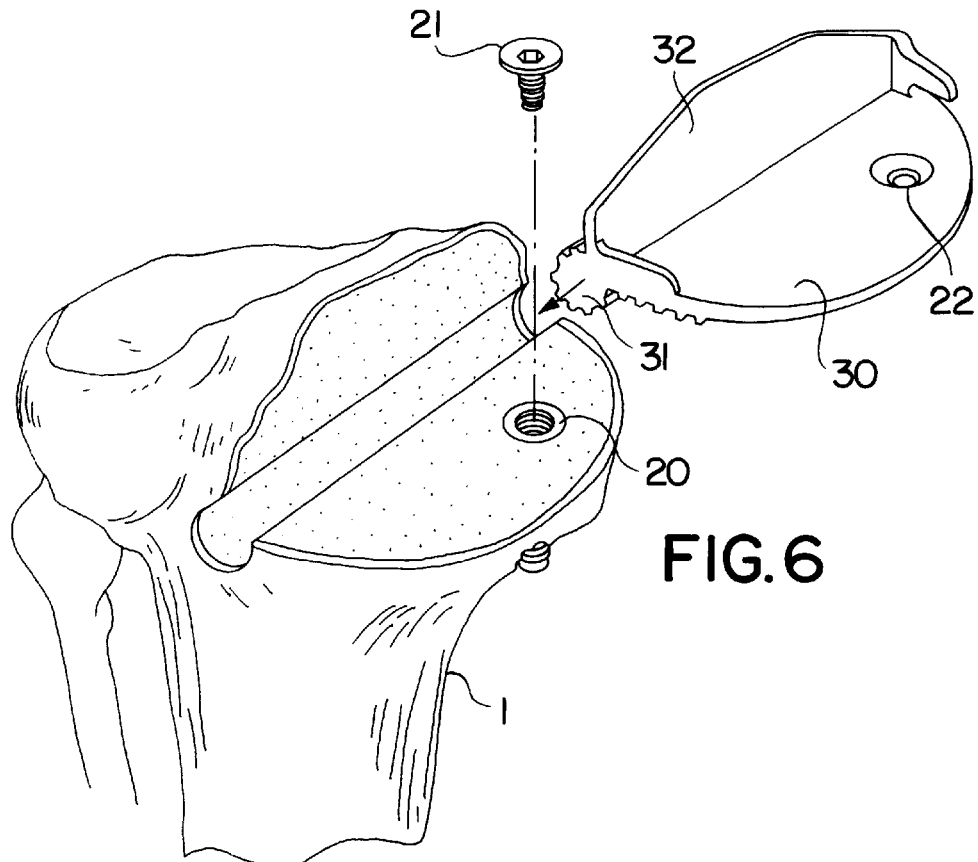
FIG. 6 depicts the main part of the prosthesis being inserted into the prepared knee joint, a screw fixture already having been inserted into and through the bone.
Figure 7:
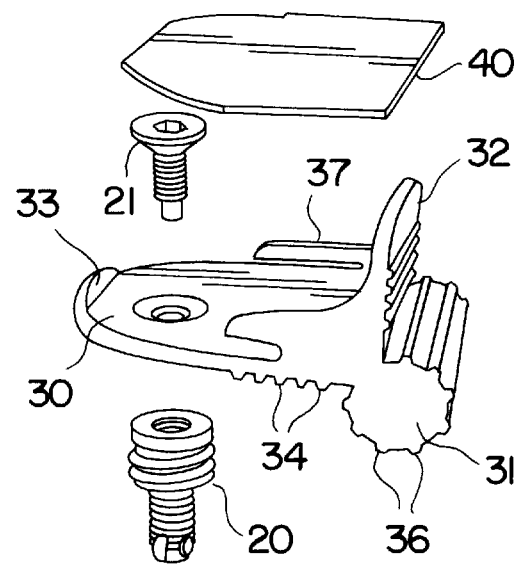
FIG. 7 shows the screw fixture, the plate-like element with elongate fixture, fixing screw, bearing plate and sliding element which together constitute the set of elements of the prosthesis.
Figure 10:
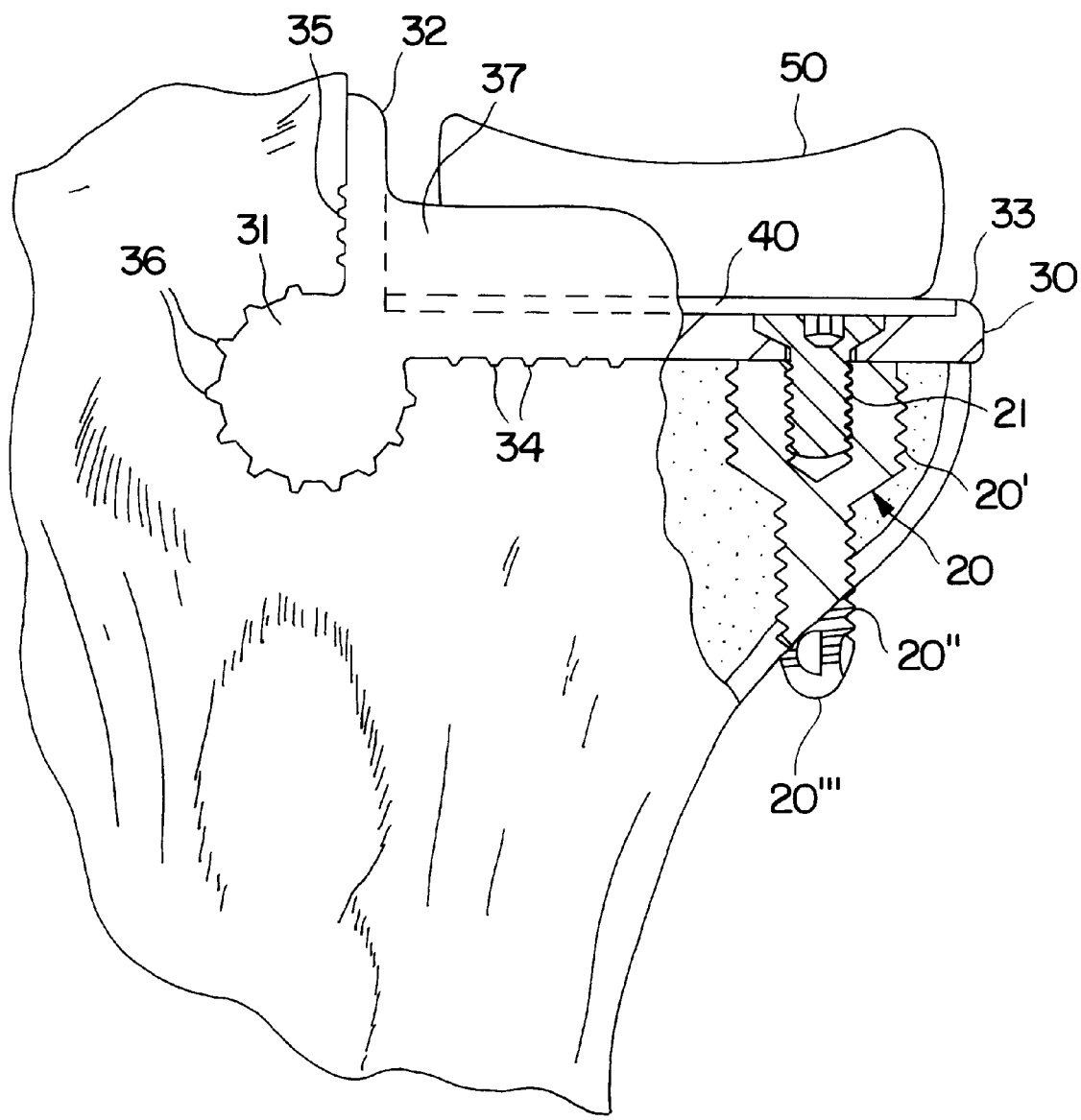
FIG. 10 depicts a part sectional view through the uni-condylar prosthesis after fitting.

A double operation drilling sequence is now required to allow insertion of the screw fixture 20 shown in position in FIG. 6. This screw fixture has the purpose of providing a threaded bore for a screw 21 which is inserted into the horizontal plate-like element of the prosthesis via a hole which has been countersunk from the top of the plate and thereby holds in position the plate like element of the prosthesis. With reference to FIG. 10, one can more easily appreciate the double drilling operation. A small diameter hole is first drilled to receive the lower threaded portion 20" of the fixing screw 20. Then, in a second operation, a larger diameter drilling is made to receive upper threaded portion 20' of the fixture 20. It is important that the first drilling operation passes through both the soft part of the bone (cancellous bone) and the hard exterior surface (cortical bone) such that the screw fixture 20 passes all the way through the outer surface. As can be seen, a sloping surface is normally provided between the upper 20' and lower 20" sections of the drilling.

The tibia is now ready for insertion of the screw fixture 20, into the hole foreseen therefor. The screw fixture is normally constructed from commercially-pure titanium and is self-tapping, the cutting surfaces of this fixture being visible for example on the thinner end of the fixture, just protruding through the cortical bone. The end 20''' of the fixture 20 is rounded, as are also at least the lower exposed threads. This ensures that, once fitted, no damage will occur to the surrounding tissue due to a sharp surface of the screw fixture which extends all the way through the outside of the bone such that the threaded portion of the fixture is visible.

Once the fixture 20 has been inserted, the prosthesis plate-like portion 30 with combined elongate fixture element 31, which has already been manufactured prior to performing the operation, is inserted such that the countersunk hole in the plate-like part 30 of the prosthesis lines up with the bore of the screw fixture 20. The screw 21 can then be inserted through the countersunk hole and into the screw fixture. The screw is then tightened to hold the plate/fixture 30, 31 of the prosthesis in position. It should be noted here that the countersunk hole will have been drilled, prior to the operation, in either an area of the plate-like element not having splines or serrations or one which does have splines or serrations. The most preferred form would however be one where the hole is in an area without serrations or splines.

Whilst one embodiment of the plate-like element (30) and fixture element (31) have been illustrated it will be clear to the reader that a prosthesis is also covered by the invention, in which no splines or serrations are present. Moreover, whilst in the uni-condylar embodiment the tube-like fixture element (31) is depicted as being directly attached to the plate-like element it would also be possible to connect the two elements 30 and 31 via a continuous rib or series of posts forming a discontinuous rib (as is explained hereinafter with reference to a bi-condylar prosthesis).

As can be seen from FIGS. 6 and 10 for example, the top of the screw fixture is substantially flush with the upper surface of the bone (i.e. surface 3") before insertion of the plate 30 and fixture 31. Whilst this flush relationship can be achieved by using a level surface prior to fitting of the plate/fixture 30, 31, this is only the case if the screw hole in the plate-like element 30 is located in an area where there are no splines or serrations laterally (i.e. in the direction of insertion) of the hole. It is thus preferred that the screw hole will be located in an area of the plate without splines or serrations. However, for the case that the screw hole is located in an area having splines or serrations, the screw fixture will be screwed down into the bone far enough so that its upper surface is below the deepest part of the serrations cut in the surface 3" of the bone. The plate/fixture 30 will then be inserted, the splines 34 passing unhindered over the top of the screw fixture and then the screw fixture may be slightly unscrewed, through the hole in the plate 30, to become flush with the upper surface 3" of the bone.

During sliding of the plate/fixture 30, 31 into position, the plate-like portion 30, dimensioned with respect to the prepared bone surface for this purpose, will be in good frictional engagement with the bone (a type of interference fit) and will cause a minor pretensioning of the bone thereby. This fitting relationship greatly contributes to the improved stability of the prosthesis.

After insertion, the prosthesis will be a tight fit in the specially prepared tibia, such that the spline or serrated grooves cut for the prosthesis will be in close contact with the corresponding splines 34, 35 and 36 of the prosthesis element, which can best be seen in FIGS. 7, 8, 9 and 10. The upstanding portion or flange 32 will then lie against the vertical filed-flat bone surface 3' of the tibia and the lower surface of the plate 30 lies against the horizontally prepared surface 3".

The arrangement of the splines/serrations on the various surfaces gives a large increase in the surface area available for osseointegration and, in addition, the provision of the splines 36 on the elongate fixture element has the particular advantage that torsional or rotational forces caused by movement of the plate 30 are possible without loosening of the joint or having a detrimental effect on the osseointegration process, since a large surface area is available for absorbing the force and allowing a large area of the bone tissue to elastically deform. A similar, although not quite as stable an effect, is possible with an elongate fixture element having no splines or serrations since the fixture has been inserted into an area of healthy bone, providing good integration but the splined version is more preferable of course since less stress is applied to each point of integration.

Having fitted the prosthesis plate part 30, the screw 21 is added and tightened. The next step in the procedure is to fit a bearing plate 40 (see FIG. 10) on to the upper surface of the plate 30. The bearing plate provides a smooth upper surface on which the sliding element 50 (a type of artificial meniscus) can slide, and consequently the bearing plate 40 will normally be made of a material such as Chromium/Cobalt alloy, Chromium/Cobalt/Molybdenum alloy or possibly a ceramics material. However the choice of material is of course not limiting for the scope of the invention, although the above mentioned materials are examples of suitable alternatives. The bearing plate 40 is held in position on the plate 30 at its front end by means of a smaller projection or flange 33 which will be approximately flush with the top surface of the bearing plate 40 when this is fitted. This is shown in FIG. 10 for example. Laterally, the plate 40 is held in position by the lower part of further projections or possibly flanges 37, the flanges 37 also having the purpose of limiting, but not preventing lateral movement of the sliding element 50 (to be added subsequently).

It must be ensured that the bearing plate 40 does not slip out of position when in normal use and, whilst the forces applied to it will generally be such that it will be kept in place, it is preferable that the bearing plate 40 is arranged to be a snap-fit on the plate 30 in between the upstanding flange elements 32, 33 and 37.

The aforementioned sliding element 50, of a durable plastics material (such as for example ultra high molecular weight polyethylene), is then placed on top of the bearing plate 40. Its position can be seen in FIG. 10 for example. The sliding element 50 is proportioned such that its dimensions in the horizontal plane (in all directions) are less than the bearing plate 40, thus allowing the sliding element 50 to be able to slide on the surface of plate 40 to allow movement in the medial/latero and anterio/posterio directions (or a combination of both) to occur to a limited extent in the knee. As is visible from FIG. 7 for example, the upper surface 51 of the sliding element 50 is dished, possibly spherically dished, so as to provide a bearing surface with lateral and longitudinal support for a condyle of the femur.

Figure 8:
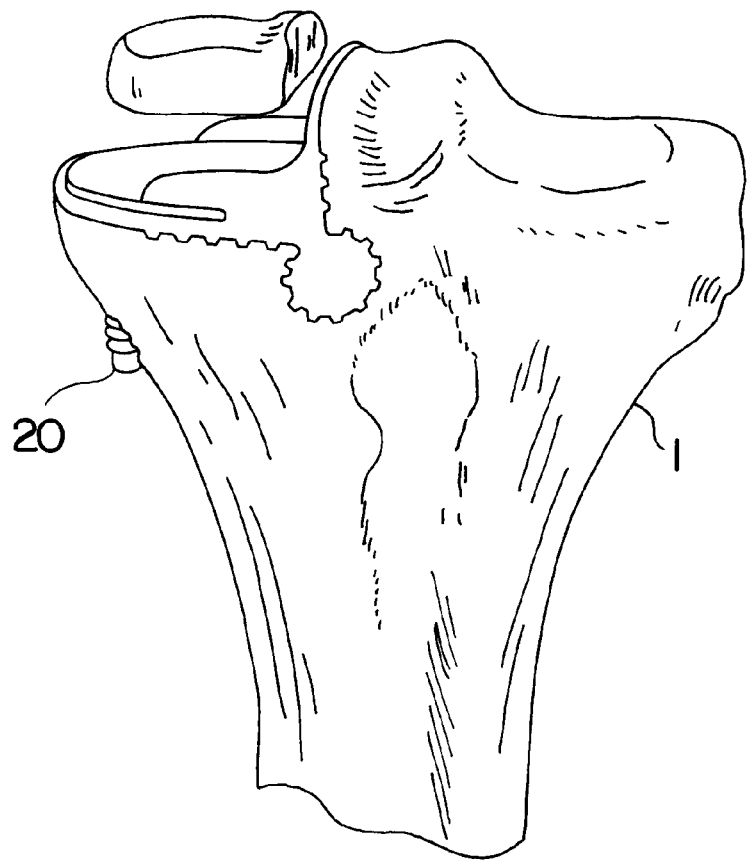
FIG. 8 shows the uni-condylar prosthesis in position.

The tibia side of the prosthesis is now ready. This ready state is depicted in FIGS. 8 and 10 for example.

Regarding some particular structural features of the prosthesis, it should be mentioned that the various metal parts of the prosthesis and in particular the main body of the prosthesis including the plate 30, tube-like fixture 31 and flange 32 are normally constructed of commercially pure titanium as are also the screw fixture 20 and screw 21. This material is chosen not only for its well-known mechanical properties but also because it has been found to be possibly the best implant material which is well adapted to osseointegration. However it is clear that any materials) suitable for osseointegration can be used.

Figure 9:
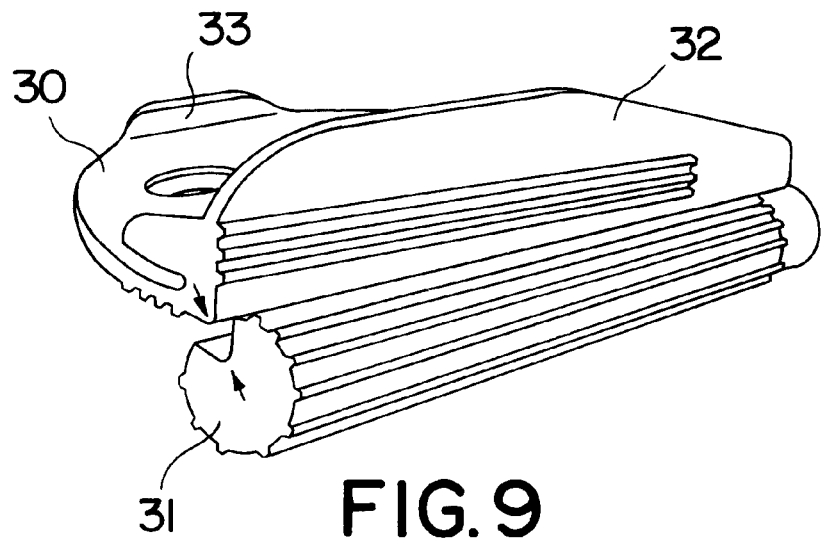
FIG. 9 depicts, from a rear and side view, the plate-like element and an elongate cylindrical fixture element before attachment of one to the other at the point of fabrication.

As shown in FIG. 9, the main body of the prosthesis can be formed in two sections, the plate portion and the elongate fixture portion which are then attached together normally by welding and often by laser welding. Due to the highly reactive nature of molten titanium an inert atmosphere during welding is then generally required.

One particular advantage of this operative technique and prosthesis for replacing a single condyle is that the cross ligaments in the knee joint do not have to be removed for preparing the knee or for fitting the prosthesis. This is of course a consequence of the fact that the hole 2 is bored from the front of the knee (from the rear is possible but the large concentration of nerves would make this awkward) and that the knee ligaments are attached at a point which lies outside of the removed quadrant. Clearly the fewer parts of the joint that are disturbed, the better in terms of healing time and effectiveness.

The prosthesis with the spline/serrated connection as described has been found to increase the surface area of contact with the bone by some 200% or more, depending on the depth of splines or serrations of course and this is one of the main reasons for improved stability and longevity.

Whilst it is clear from the aforegoing that a good fit of the parts is ensured by accurate matching of the surfaces of the plate/fixture/flange/splines etc., it is nevertheless contemplated that a set of, for example, five different standard size prosthetic elements would be available (i.e. five sets of plates 30 etc. of differing sizes) and that the most appropriate elements for each patient would be selected after preoperative (e.g. X-ray) examination. Thus although FIG. 10 for example shows a fitted prosthesis with the plate-like part 30 meeting exactly with the end of the bone, it could be that there will be some minor difference. However, this is not of great importance.

FIGS. 11 to 13 and FIG. 14 show two different embodiments of a whole-joint or bi-condylar prosthesis. Unless otherwise stated, it will be clear to the reader that the principles and advantages applicable to the uni-condylar prosthesis are valid for the bi-condylar prosthesis. Hence the general principles, for example for filing the spline/serrated grooves and the possible selection of materials, and general element shapes used are the same.

The reference numerals used for describing the bi-condylar embodiments are similar to those used for the uni-condylar type except that 100 is added. Hence e.g. 2 becomes 102, 50 becomes 150.

The preparation and fitting of the prosthesis occurs, as in the uni-condylar example, during one operation only but the operation requires cutting away the cross ligaments to perform the operation, since they are attached to the section to be removed.

Figure 11:
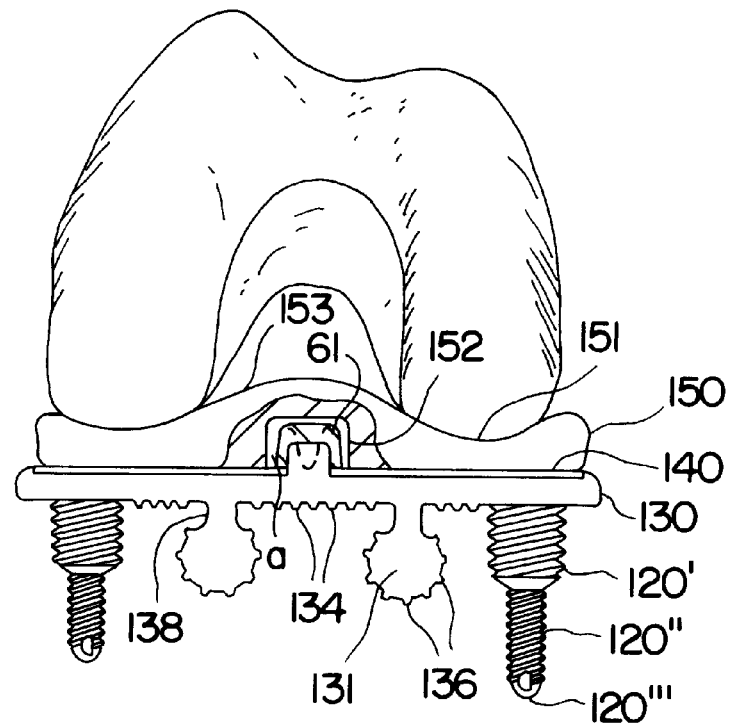
FIG. 11 depicts another embodiment of the invention which concerns a bi-condylar prosthesis, the tibia having been removed for clarity and the femur being depicted.
Figure 12:
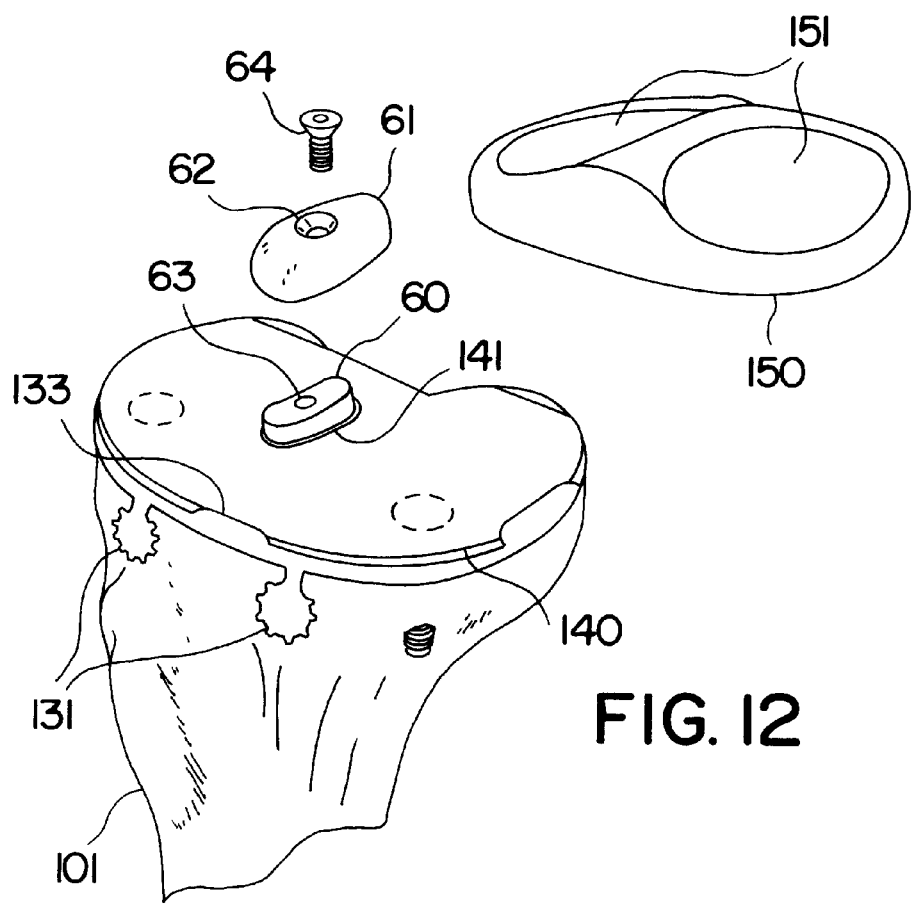
FIG. 12 shows a view of FIG. 11 before the keel element is attached to the keel-fixture and before the sliding element is applied over the top.
Figure 13:
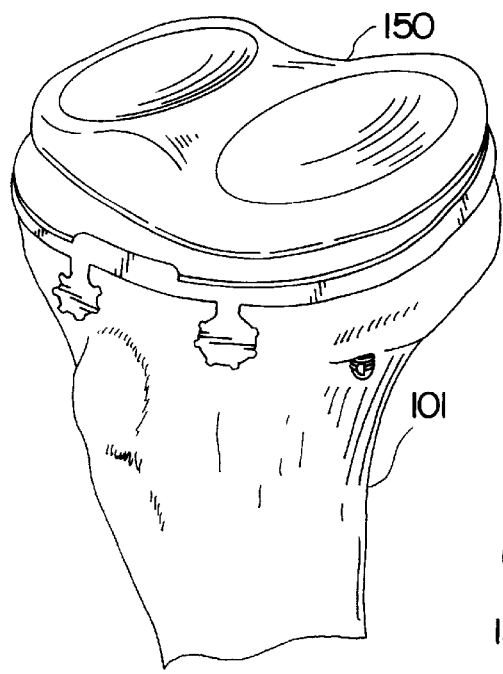
FIG. 13 depicts the sliding element in position over the keel and partly shows the freedom of movement which the sliding element has.

Taking the embodiment in FIGS. 11 to 13 for example, the bone at the top part of the joint is cut off to be substantially horizontal in normal use when the foot is flat on the ground. Similar tools to those used in FIG. 5(a), (b) and (c) are used to file the surfaces flat and to provide the drilled holes and the tibia upper bone surface with the appropriate spline or serrated grooves, although clearly two elongate extensions on each tool would be applied for fitting in the two drilled holes of this embodiment whereas only one elongate extension would be necessary with the embodiment of FIG. 14 for example.

A further operative process is required however in that the bone upper surface, after having been cut, must be slotted to allow passage of the connecting portions 138 between the spline/serrated elongate fixtures 131 and the plate 130. A slot 102' of the type required and an example of a continuous connecting portion 138 like a connecting rib are shown in connection with the single fixture element embodiment in FIG. 14. Clearly the continuous portion 138 could also be a series of vertical connection portions, like small posts (i.e. a discontinuous rib connection), if this was desired and this is often thought useful since the bone can grow between the posts and thus this possibility assists osseointegration due to the larger surface area of contact for integration.

Having prepared the bone surfaces, the bone is then drilled vertically through each remaining portion of the condyles, in a two stage process so as to provide holes of different diameters for accepting the screw fixtures 120 which have outer threaded portions 120' and 120" of differing diameters as in the first example.

Figure 14:
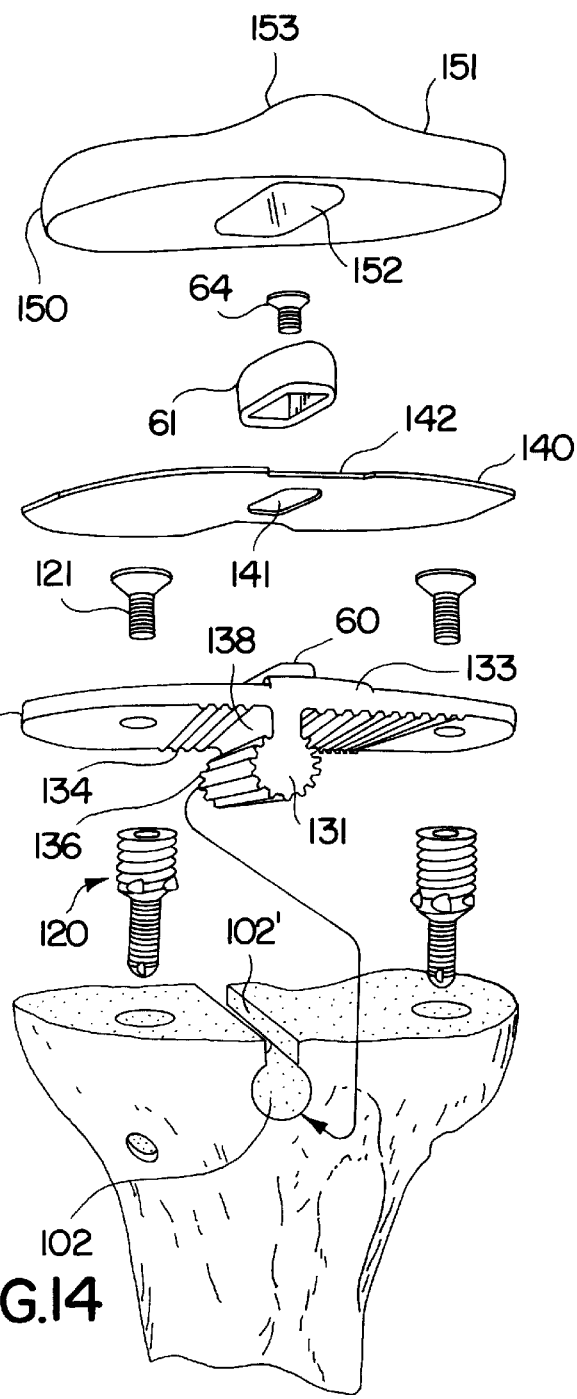
FIG. 14 shows an exploded view of a further bi-condylar prosthesis having only one elongate fixture and the tibia bone prepared to receive said prosthesis.

Each of the screw fixtures are fitted and project through the hard bone surface in a manner corresponding to the first mentioned example. The prepared plate 130 foreseen with two tube-like serrated fixture elements 131 is slid into place over the upper surface of the bone until both screw fixture holes line up with the countersunk holes in the plate 130. The screws 121 are fitted and tightened. It is noted here that, as in the uni-condylar example, each of the screw holes in the plate 130 are normally placed outside the area of the plate 130 which contains the splines/serrations 134 (although they could be inside this area, which would again require a similar operation of unscrewing if one wished to obtain a flush surface of the screw fixture as described in connection with the uni-condylar example). This can be seen for example in FIG. 11. The plate 130 also differs in that an upstanding keel-fixture 60 (not present in the uni-condylar type) having a prepared threaded hole 63 is integrally formed on its upper surface. This keel would normally be formed centrally but of course could be off-centre as shown in FIG. 14 for example. In fact due to the non-symmetrical nature of the condyles of the tibia the non-symmetrical plate would be more common. Indeed the upper surface of the plate 130 would in any case almost always be asymmetrical. The shape of the cross-section of the keel fixture could be oval as shown, although other shapes are obviously possible.

Whilst the keel fixture is described above as "formed" on the upper surface, this expression also includes the possibility where the fixture is formed separately and then attached onto the plate by whatever means as long as the function of course is unaltered.

After the plate has been slid into position, the bearing plate 140 is snap-fitted or otherwise fitted to the prepared plate upper surface. The upper surface may of course include flanges, other projections or the like for forming a "lateral" holding means for the bearing plate 140.

The plate 140 also has a cut away portion 141 proximate the mid portion of the plate 140 which fits closely over keel-fixture 60, thus providing additional positional locating means. When the plate 140 has been fitted, a keel 61 with countersunk hole 62 is added over the top and the screw 64 is tightened thus holding the assembly firmly together.

A sliding element 150 of smaller dimensions than the upper area of the bearing plate 140 is fitted over the bearing plate to bear on it from above. The sliding element 150 is again of a suitable plastics material (e.g. UHMWPE) and has a recess 152 in its lower surface which accommodates the keel 61 with some amount of free play in the horizontal plane (i.e. in the medial/latero and anterio/posterior directions or a combination of both). However movement vertically is not possible. This free play has been shown as "a" in FIG. 11 and allows the sliding element 150 to float over the plate 140 surface by a limited amount, but still constrains it at the limits. The sliding element 150 also includes a shaped upper surface with two, possibly spherically, dished upper recesses and a raised mid portion 153.

As shown in FIG. 11 the femur condyles "fit" into each of these dished parts and of course the contour of the dished surface must be adequately matched to the femur condyles. The femur may not need a prosthetic replacement itself but this possibility is of course totally compatible with either the uni- or bi-condylar type of tibia replacement of this invention.

The sliding element 150 in position on top of the bearing plate 140 is shown in FIG. 13. This Figure also shows the sliding element in a position where the free play "a" (in FIG. 11) is has allowed the sliding element 150 to move in order to leave a gap at the front left hand side (as depicted) of the tibial prosthesis.

The embodiment of FIG. 14 is a more preferred embodiment of the bi-condylar prosthesis, since only one hole 102 and one slot 102' need to be drilled and cut respectively in the sawn-off tibial bone. The elongate fixture element 131 is clearly shown not central in this drawing and there are more splines on one side than on the other due to this relationship. In particular this is not merely due to the asymmetrical nature of the top of the tibia but also since a fixture which is offset from the plate 131 centre in the medial/latero direction will allow that the drilling and fitting of fixture element 131 will not interfere with the knee cap.

As before, once cut and filed appropriately (in accordance with the manner described previously), the plate 130 is inserted along with the fixture 131 and joint 138 into position on the prepared bone, having screw fixtures 120 (previously described) already fitted therein. As also mentioned previously, a type of interference fit (in the order of a few hundredths of a millimeter) will occur thus giving a certain pretensioning of the bone surface and ensure a tight fit, which will lead to more rapid integration due to the minimal movement of the prosthesis that is possible. Slight vertical movement of the end of the plate 130 (i.e. rotational movement about the elongate fixture(s) which functions as a rotational centre) on either side is reacted by the splines 136, so that even where the prosthesis is not a perfect fit the splines anchorage in the bone will not cause loosening of the joint or have a detrimental effect on the osseointegration process. As stated previously also, the provision of splines or serrations is not essential but a larger surface area for absorbing the aforementioned rotational forces is provided.

Visible in this Figure, but also applicable equally to the previous embodiments, is the bearing plate 140 with recessed edge shown at 142 so as to fit flush with the forward flange 133 of the plate 130. Similar recesses or flattened edges can be foreseen in addition or alone at the medial/latero edges of the plate 140 if this is felt necessary, although the keel fitting 60, 61 provides sufficient medial/latero stability in most cases such that such flanges on the plate 130 may not be necessary.

The screws 121 are fitted and the bearing plate 140 fitted into place over the keel fixture 60. The keel is consequently fixed in position with the aid of screw 64 and the sliding element 150 fitted.

A further advantageous embodiment of a bi-condylar prosthesis is illustrated in FIGS. 15 to 19. The main difference between this embodiment and the bi-condylar prostheses described above is that the elongate fixtures in this embodiment are designed to be oriented at an angle to the sagittal plane when the prosthesis has been implanted in the tibia, whilst the elongate fixtures in the above embodiments are designed to be oriented in parallel to the sagittal plane when implanted.

For the sake of simplicity, only the features that are different from the previous embodiments will be described in the following description. The prosthesis thus for instance can be provided with splines or not be provided with splines or be provided with one assymmetrically located elongate fixture or two more or less symmetrically located elongate fixtures.

All parts not described in detail, such as bearing plate or sliding elements etc, may be similar to the parts used in the above embodiments.

Figure 15:
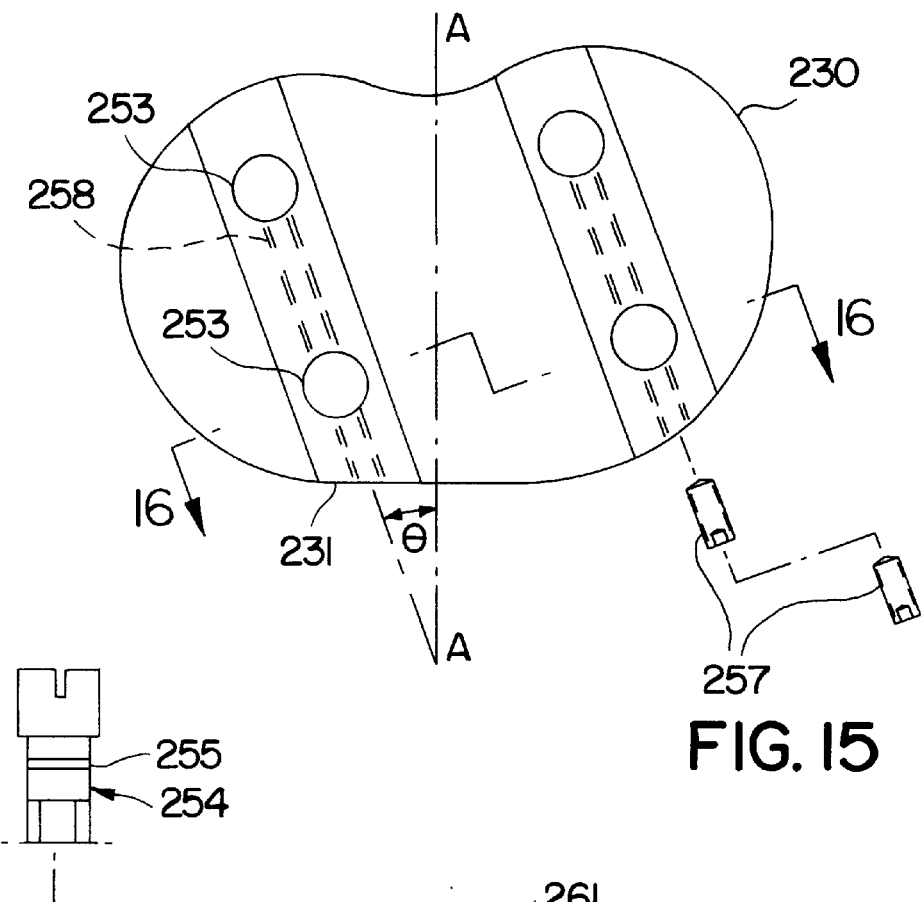
FIGS. 15, 16 and 17 depict two views of another preferred embodiment of a bi-condylar prosthesis having two elongate fixtures, FIG. 16 showing a section along the line B—B in FIG. 15.
Figure 16:
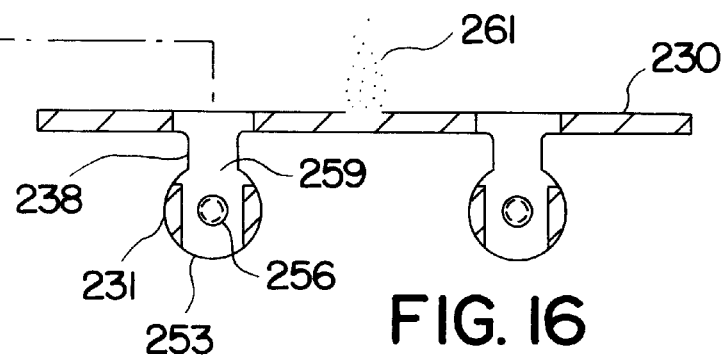
Figure 17:
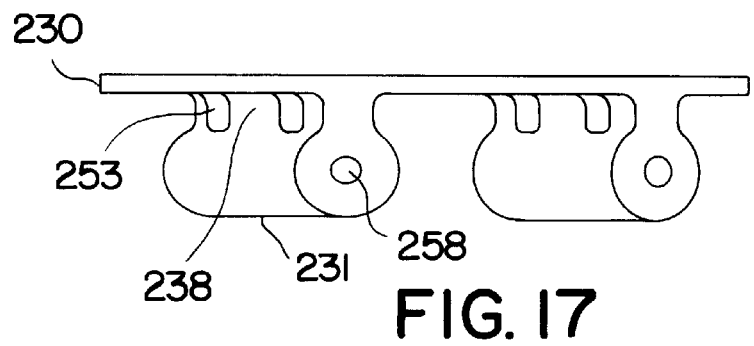

The prosthesis in the embodiment according to FIGS. 15–17 thus comprises a plate 230 provided with two tubelike, elongate fixtures 231 which are attached to the plate 230 by means of a connecting portion 238. The plate 230 also is provided with bore-holes 253 for attachment screws 254 going through the connecting parts 238 and the fixtures 231. This location of the holes 253 will allow the bores to be countersunk (at 259) to an extent sufficient to ensure that the head of the screws 254 does not interfere with with the upper surface of the plate 230. The screws 254 are provided with a circumferential groove 255 and the fixtures 231 are provided with a longitudinal, threaded bore 256 extending from one end across one bore 253 to the other bore 253. By means of this bore and groove, the screws 254 can be locked by means of lock screws 257 screwed into the bore 258 into engagement with the groove 255. The function of these bore-holes and attachment screws is to lock the prosthesis against movements, primarily during the healing period.

The line A—A indicates the orientation of the sagittal plane when the plate 130 has been slid onto the tibia. As indicated in FIG. 15, the longitudinal direction of the fixtures form an angle θ with the line A—A. The angle θ may vary between 5° and 45°, but preferably is between 15° and 35°, most preferably 20°–30°. In the embodiment illustrated, the angle θ has been chosen to be 20°.

There are several advantages connected with this design. One important advantage is that the access to the knee joint is greatly facilitated. The fact that the fixtures are to be obliquely oriented relative to the sagittal plane means that all cutting and drilling operations can be performed from the ventral side of the proximal part of the tibia after cutting the anterior cruciate ligament without interfering with the patella since the patella and the ligamentum patellae easily can be pushed aside. Apart from this, the operation is essentially performed in the same way as the operation for implanting the embodiments according. to FIGS. 11–14. When the implant has been slid into place, the holes for the attachment screws can be drilled into the bones through the holes 253 in the plate 230 and the screws 254, which preferably are self-tapping screws, can be screwed into the bone. The inner screw 254 of course has to be locked by its respective lock screw 254 before the outer screw 254 is inserted.

In this context it should perhaps be pointed out that the positioning of the attachment holes to the fixtures and the connecting portion as described here also is possible in the embodiments according to FIGS. 11–14.

Another important advantage of this embodiment is that the prosthesis will have a greater stability against movements during the healing period. The plate 230 will be subjected to forces oriented in the sagittal plane during the normal articulation movements of the knee joint, since these movements mainly will be oriented in the sagittal plane. The fixtures will however largely take up these forces due to their oblique orientation relative to the sagittal plane. This means also that the attachment screws 254, although useful in some applications, are not strictly necessary.

The upper, cut surface of the tibia will also be less disturbed and consequently have a better fit against the under side of the plate 230 since no fixtures (20, 120) for anchoring the plate are necessary. Another consequence is that the contact area between plate and tibia will be larger and that the risk that to much of the load on the plate is taken up by the fixtures is lessened. This in turn will enhance the osseointegration and lessen the risk for bone resorption.

The rotational movements of the plate around the elongate fixtures will also be counteracted to a larger extent since the distribution of the load acting on the plate 230 will be more balanced and the rotational movements, if any, will be deflected to an axis located in or along the oblique elongate fixtures.

Figure 18:
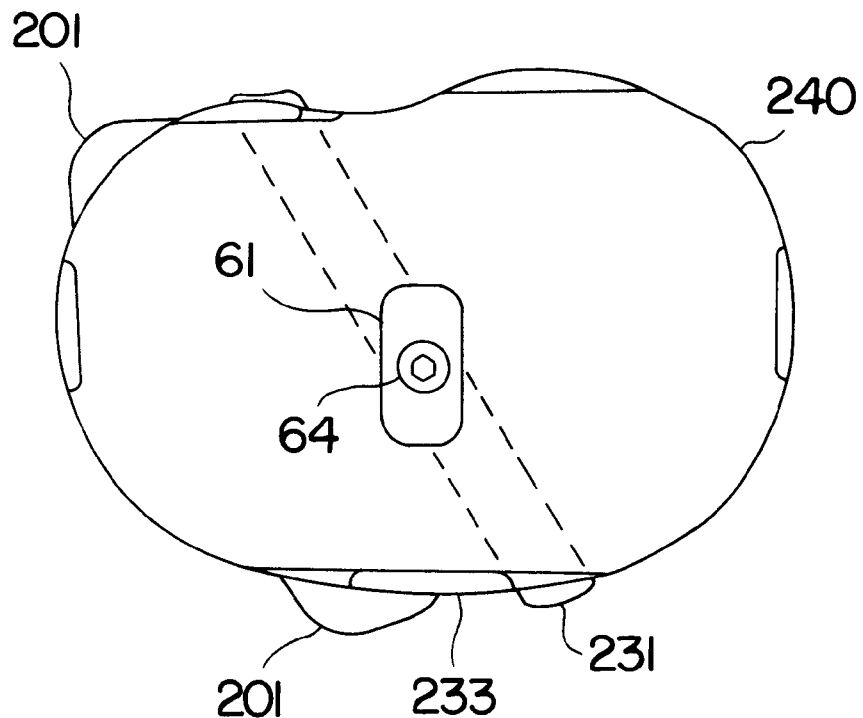
FIGS. 18 and 19 depict two different views of a bi-condylar prosthesis similar to the one shown in FIGS. 15–17, but having only one elongate fixture.
Figure 19:
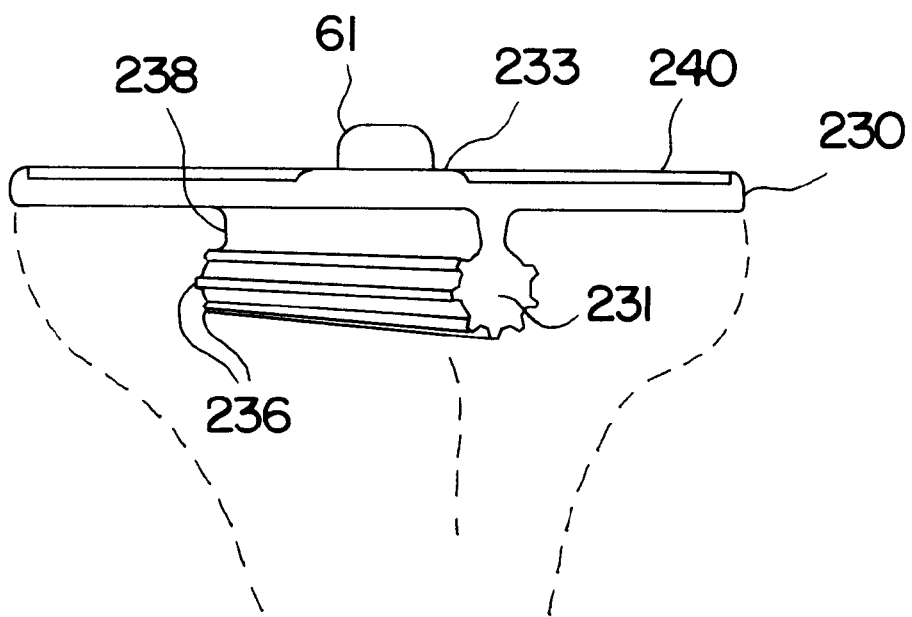

The embodiment according to FIGS. 18 and 19 differs from the above embodiment in that only one elongate fixture is provided. The reference sign 230 thus denotes the plate, 231 the elongate fixture, 233 the flange holding the bearing plate 240, 236 denotes splines on the elongate fixture, 201 the tibia and reference signs 61 and 64 the parts holding the bearing plate 240.

The advantages of this embodiment are largely the same as the advantages of the embodiment according to FIGS. 15–17. It should however be noted that there generally is less need for fixtures or attachment screws in the bi-condylar versions of the invention than in the uni-condylar versions.

Whilst particular embodiments have been described it is understood that the said embodiments should not be construed as limiting for the scope of the invention which is defined in the claims appended hereto.

What is claimed is:

1. A joint prosthesis for permanent anchorage in the bone tissue at the joint end of a first articulatory part of a joint, especially a knee joint, in the human body, said joint defining a predetermined main articulation plane in which articulatory movements of said joint take place said joint prosthesis comprising:

a flat, plate-like element having front and rear major faces, the rear major face adapted in use to engage with a complementary bone surface which presents the joint end or a part of the joint end of the first articulatory part after resection of the original joint end or a part of the original joint end, and at least one elongate fixture which extends along the plate-like element at a spaced distance therefrom and is attached to the rear major face of the plate-like element so as to allow the at least one elongate fixture in use to be located in healthy, relatively intact bone, wherein the plate-like element and at least one fixture are integrally formed into a main body component prior to anchorage in the bone tissue, and wherein said at least one elongate fixture is so arranged relative to the plate-like element that on anchorage of the joint prosthesis in the bone tissue at the joint end of the first articulatory part said at least one elongate fixture is inclined at an angle relative to said predetermined main articulation plane.

2. A joint prosthesis according to claim 1, wherein the or each elongate fixture is oriented along a plane forming an angle of about 15° to 45° with the predetermined main articulation plane.

3. A joint prosthesis according to claim 1, wherein the or each elongate fixture is oriented along a plane forming an angle of about 15° to 35° with the predetermined main articulation plane.

4. A joint prosthesis according to claim 1, wherein the or each elongate fixture is oriented along a plane forming an angle of about 20° to 30° with the predetermined main articulation plane.

5. A joint prosthesis according to claim 1, wherein the or each elongate fixture is provided with splines or serrations on the outer surface thereof.

6. A joint prosthesis according to claim 1, wherein the rear major face of the plate-like element presents splines or serrations which extend in a direction substantially parallel to the axis of the at least one elongate fixture.

7. A joint prosthesis according to any of claims 1–6, wherein the plate-like element is provided with one or more apertures which extend therethrough from the front major face to the rear major face and are countersunk from the front major face, wherein the plate-like element and the at least one elongate fixture constitute a main body component part of the joint prosthesis and the joint prosthesis further comprises an anchoring screw for each aperature, the or each anchoring screw adapted in use to project through the associated aperture to anchor the main body component part to the joint end of the first articulatory part of the joint.

8. A joint prosthesis according to claim 7, wherein the rear major face of the plate-like element presents splines or serrations which extend in a direction substantially parallel to the axis of the at least one elongate fixture and wherein the or each aperture in the plate-like element is positioned so as to open in the rear major face of the plate-like element in an area which is free from splines or serrations.

9. A joint prosthesis according to claim 7, wherein the joint prosthesis comprises one or more self-tapping screw fixture elements for implantation in the bone tissue at the joint end of the first articulatory part of the joint and that the or each anchoring screw has a threaded shank which is adapted in use to project through the associated aperture and be received in a threaded bore presented by the screw fixture element or one of the screw fixture elements.

10. A joint prosthesis according to claim 9, wherein the or each screw fixture element comprises two integral cylindrical portions of different diameter and is provided with a substantially flat front face in which the threaded bore opens and an external screw thread for fixing the screw fixture element in the bone tissue at the joint end of the first articulatory part of the joint.

11. A joint prosthesis according to any of claims 1–6, wherein the or each elongate fixture is offset from and attached to the rear major face of the plate-like element by one or more rib elements, that the plate-like element, rib element or elements and elongate fixture or fixtures constitute a main body component part of the joint prosthesis, that one or more apertures are provided in the main body portion, the or each aperture extending rearwardly from the front major face of the plate-like element through one of the rib elements and the associated elongate fixture and that the joint prosthesis further comprises an anchoring screw for each aperture, the or each anchoring screw receivable in the associated aperture to anchor the main body component part to the bone tissue at the joint end of the first articulatory part of the joint.

12. A joint prosthesis according to claim 11, wherein the or each elongate fixture is provided with an axial screw threaded bore and the joint prosthesis further comprises one or more lock screws for location in each axial screw threaded bore, the or each lock screw adapted in use to act on one of the anchoring screws to lock the anchoring screw in position.

13. A joint prosthesis according to claim 1, wherein the joint prosthesis comprises one elongate fixture which is attached to the rear major face of the plate-like element substantially in the mid-portion thereof.

14. A joint prosthesis according to claim 1, wherein the plate-like element has a keel-fixture depending from the front major face thereof, said keel-fixture being approximately centrally positioned on the front major face of the plate-like element.

15. A joint prosthesis according to claim 14, wherein the joint prosthesis comprises (i) a flat bearing element having front and rear major faces and an aperture which extends therethrough from the front major face to the rear major face to enable the bearing element to fit over the keel-fixture and the rear major face of the bearing element to sit flat against the front major face of the plate-like element, and (ii) a keel having a rounded frontal face and a recessed rear face and which is adapted in use to be fixedly attached to the keel-fixture to secure the bearing element in position on the plate-like element against vertical displacement.

16. A joint prosthesis according to claim 15, wherein the joint prosthesis comprises a sliding element adapted in use to sit on the front major face of the bearing element, the sliding element having a dished, for example spherically dished, frontal face for co-operation with the joint end of a second articulatory part of the joint.

17. A joint prosthesis according to claim 16, wherein the sliding element is made of ultra high molecular weight polyethylene.

18. A joint prosthesis according to claim 16, wherein the sliding element is provided with a recess in its rear face for receiving the keel, said recess being larger than the keel to allow a limited float of the sliding element across the bearing element front major face.

19. A joint prosthesis according to claim 15, wherein the bearing element is made from a Cobalt/Chromium alloy, Cobalt/Chromium/Molybdenum alloy or a ceramics material.

20. A joint prosthesis according to claim 19, wherein the other elements of the joint prosthesis are made from commercially pure titanium.

21. A joint prosthesis according to claim 1, wherein said prosthesis is adapted for fitting in one operation only.

22. A joint prosthesis according to claim 1, wherein the plate-like element and each elongate fixture are manufactured as an integrally formed main body component.

23. A joint prosthesis according to claim 1, wherein the plate-like element and each elongate fixture are manufactured as separate pieces that are adapted to be integrally formed into the main body component prior to anchorage in the bone tissue.

* * * * *